(12) United States Patent
Ostrowski

(10) Patent No.: US 7,472,797 B2
(45) Date of Patent: Jan. 6, 2009

(54) CONTAINER FOR COLLECTING AND STORING BREAST MILK

(75) Inventor: Mark Ostrowski, Greenville, SC (US)

(73) Assignee: Capitol Vial Inc., Auburn, AL (US)

(*) Notice: Subject to any disclaimer, the term of this patent is extended or adjusted under 35 U.S.C. 154(b) by 45 days.

(21) Appl. No.: 11/191,301

(22) Filed: Jul. 27, 2005

(65) Prior Publication Data
US 2006/0025718 A1  Feb. 2, 2006

Related U.S. Application Data

(60) Provisional application No. 60/591,897, filed on Jul. 28, 2004.

(51) Int. Cl.
B65D 55/16 (2006.01)
B65D 41/18 (2006.01)
B65D 39/00 (2006.01)
B65D 53/00 (2006.01)
B65B 7/28 (2006.01)
A61M 1/06 (2006.01)

(52) U.S. Cl. .............. 215/306; 215/230; 215/344; 215/44; 215/45; 215/235; 220/839; 220/792; 220/375; 220/793; 604/74

(58) Field of Classification Search ............ 215/306, 215/345, 235, 11.1, 43, 44; 220/375, 837, 220/839, 288, 793; 604/74, 346; 141/18, 141/383, 384, 22
See application file for complete search history.

(56) References Cited

U.S. PATENT DOCUMENTS 1,050,706 A  1/1913  Taylor
2,711,840 A  6/1955  Gits et al.
2,814,404 A  11/1957 Towns
2,814,405 A  11/1957 Edwards
2,852,054 A  9/1958  Motley
3,172,130 A  3/1965  Lange (Continued)

FOREIGN PATENT DOCUMENTS

WO  PCT/US93/12490  12/1993

OTHER PUBLICATIONS

International Searching Authority, International Search Report and Written Opinion of the International Searching Authority, Mar. 20, 2007, International Application No. PCT/US05/27546 (13 pages).
International Searching Authority, International Search Report and Written Opinion of the International Searching Authority, Mar. 26, 2007, International Application No. PCT/US05/27929 (11 pages).

Primary Examiner—Robin Hylton
(74) Attorney, Agent, or Firm—Wood, Herron & Evans, L.L.P.

(57) ABSTRACT

A container for collecting and storing breast milk. More particularly, one embodiment provides a container for collecting and storing breast milk obtained using a breast pump, comprising: a body, wherein the body has an open end with a lip, a closed end and a cavity between the open end and the closed end for receiving therein the breast milk; a cap; a hinge disposed adjacent the open end of the body for connecting the cap to the body; a sealing mechanism disposed on the cap, wherein the sealing mechanism provides a resealable, watertight seal between the cap and the lip of the body when the cap is placed thereon; and at least one thread disposed at the open end of the body, wherein the thread is configured to provide a screw-on connection between the body and the breast pump.

21 Claims, 19 Drawing Sheets

U.S. PATENT DOCUMENTS

| | | | |
|---|---|---|---|
| 3,252,492 A | | 5/1966 | Marchant |
| 3,282,477 A | | 11/1966 | Henchert |
| 3,346,099 A | | 10/1967 | Thomas et al. |
| 3,415,361 A | | 12/1968 | Adams, Jr. et al. |
| 3,419,179 A | * | 12/1968 | Deuschle et al. ............ 220/375 |
| 3,470,930 A | | 10/1969 | Jurczenia |
| 3,592,349 A | | 7/1971 | Baugh |
| 3,786,982 A | | 1/1974 | Rakes et al. |
| 3,838,960 A | | 10/1974 | Lovejoy |
| 3,861,433 A | | 1/1975 | Schier et al. |
| 3,900,550 A | | 8/1975 | Oliver et al. |
| 3,910,740 A | | 10/1975 | Rees |
| 3,911,920 A | | 10/1975 | Susinn |
| 3,938,675 A | | 2/1976 | Rees |
| 4,082,201 A | | 4/1978 | Bittel |
| 4,157,762 A | | 6/1979 | Robinson |
| 4,180,178 A | | 12/1979 | Turner |
| 4,204,824 A | | 5/1980 | Paradis |
| 4,244,479 A | | 1/1981 | Smalley |
| 4,267,928 A | | 5/1981 | Curry, Jr. |
| 4,298,036 A | | 11/1981 | Horvath |
| 4,323,067 A | * | 4/1982 | Adams ........................ 604/74 |
| 4,351,630 A | | 9/1982 | Hayberg et al. |
| 4,375,947 A | | 3/1983 | Marcus |
| 4,377,247 A | | 3/1983 | Hazard et al. |
| 4,386,714 A | | 6/1983 | Roberto et al. |
| 4,390,111 A | | 6/1983 | Robbins et al. |
| 4,420,089 A | | 12/1983 | Walker et al. |
| 4,422,998 A | | 12/1983 | Sorensen |
| 4,540,543 A | | 9/1985 | Thomas et al. |
| 4,548,332 A | | 10/1985 | Neat |
| 4,579,246 A | | 4/1986 | Swearingen et al. |
| 4,619,373 A | | 10/1986 | Galer |
| 4,655,363 A | | 4/1987 | Neat |
| 4,713,219 A | | 12/1987 | Gerken et al. |
| 4,717,034 A | | 1/1988 | Mumford |
| 4,754,656 A | | 7/1988 | Charm |
| 4,754,896 A | | 7/1988 | Roltgen et al. |
| 4,783,056 A | | 11/1988 | Abrams |
| 4,801,011 A | | 1/1989 | Desidoigts et al. |
| 4,807,425 A | | 2/1989 | Abrams et al. |
| 4,812,116 A | | 3/1989 | Abrams |
| 4,813,570 A | | 3/1989 | Pontoppidan |
| 4,860,907 A | | 8/1989 | Sondal |
| 4,866,952 A | | 9/1989 | Hight et al. |
| 4,950,152 A | | 8/1990 | Brun, Jr. et al. |
| 4,955,413 A | | 9/1990 | Bennett |
| 5,000,204 A | | 3/1991 | Smith |
| 5,008,066 A | | 4/1991 | Mueller |
| 5,012,941 A | | 5/1991 | Abrams et al. |
| 5,020,683 A | | 6/1991 | Strassheimer |
| 5,038,454 A | | 8/1991 | Thornock et al. |
| 5,051,227 A | | 9/1991 | Brun, Jr. et al. |
| 5,108,029 A | | 4/1992 | Abrams et al. |
| 5,114,003 A | | 5/1992 | Jackisch et al. |
| 5,133,470 A | | 7/1992 | Abrams et al. |
| 5,139,165 A | | 8/1992 | Hara |
| 5,169,374 A | | 12/1992 | Abrams et al. |
| 5,199,635 A | | 4/1993 | Abrams et al. |
| 5,219,320 A | | 6/1993 | Abrams et al. |
| 5,269,430 A | | 12/1993 | Schlaupitz et al. |
| 5,358,476 A | * | 10/1994 | Wilson ........................ 604/74 |
| 5,429,699 A | | 7/1995 | Abrams et al. |
| 5,435,456 A | | 7/1995 | Dubach |
| 5,441,150 A | | 8/1995 | Ma |
| 5,474,177 A | | 12/1995 | Abrams et al. |
| 5,513,768 A | | 5/1996 | Smith |
| 5,575,399 A | | 11/1996 | Intini |
| 5,601,214 A | | 2/1997 | Hendrickson et al. |
| 5,624,528 A | | 4/1997 | Abrams et al. |
| 5,638,957 A | | 6/1997 | Braiser |
| 5,667,094 A | | 9/1997 | Rapchak et al. |
| 5,723,085 A | | 3/1998 | Abrams et al. |
| 5,875,891 A | | 3/1999 | Snell |
| 5,885,517 A | | 3/1999 | Hendrickson et al. |
| 6,050,400 A | | 4/2000 | Taskis et al. |
| 6,253,937 B1 | | 7/2001 | Anderson |
| 6,302,286 B1 | | 10/2001 | Witherspoon |
| RE37,676 E | | 4/2002 | Abrams et al. |
| 6,398,067 B1 | | 6/2002 | Belfance et al. |
| 6,413,468 B1 | | 7/2002 | Britton |
| 6,516,963 B2 | | 2/2003 | Mihashi |
| 6,530,493 B2 | | 3/2003 | Anderson |
| 6,622,882 B2 | | 9/2003 | Smith |
| 6,669,049 B2 | | 12/2003 | Crider |
| 6,705,463 B1 | | 3/2004 | Bucholtz et al. |
| 6,732,773 B2 | * | 5/2004 | Renz ........................ 141/384 |
| 6,736,628 B1 | | 5/2004 | Zuffa |
| 6,769,558 B1 | | 8/2004 | Bucholtz |
| 6,833,102 B2 | | 12/2004 | Martino et al. |
| 6,910,594 B2 | | 6/2005 | Foley et al. |
| 7,001,564 B1 | | 2/2006 | Geisinger |
| 7,004,339 B2 | * | 2/2006 | Renz ........................ 604/74 |
| 2005/0023238 A1 | | 2/2005 | Wong |
| 2006/0049550 A1 | | 3/2006 | Lin |

* cited by examiner

CONTAINER FOR COLLECTING AND STORING BREAST MILK

RELATED APPLICATIONS

This application claims the benefit of U.S. Provisional Application Ser. No. 60/591,897, filed Jul. 28, 2004.

FIELD OF THE INVENTION

The present invention relates to a container for collecting and storing breast milk.

More particularly, one embodiment of the present invention provides a container for collecting and storing breast milk obtained using a breast pump, comprising: a body, wherein the body has an open end with a lip, a closed end and a cavity between the open end and the closed end for receiving therein the breast milk; a cap; a hinge disposed adjacent the open end of the body for connecting the cap to the body; a sealing mechanism disposed on the cap, wherein the sealing mechanism provides a resealable, watertight seal between the cap and the lip of the body when the cap is placed thereon; and at least one thread disposed at the open end of the body, wherein the thread is configured to provide a screw-on connection between the body and the breast pump.

For the purposes of the present application, the term "resealable" means that the container can be opened/reopened and closed/reclosed numerous amount of times (i.e. more than 5 times) and still retain its "water-tight" properties.

Further, for the purposes of the present application, the term "watertight" means that the container passes the blue crystal dye test. The blue crystal dye test is a visual test to detect leaks within a container seal. A container "passes" the blue crystal dye test if the white paper, in which the container is placed on, does not visually change color (i.e. The white paper does not become contaminated with the blue crystal dye liquid from the container). The blue crystal dye test procedure consists of the following: (a) the blue crystal dye liquid is prepared by adding one teaspoon of blue crystal dye powder to one gallon of alcohol and then thoroughly mixing the solution; (b) the blue crystal dye liquid is poured into the container (i.e. a sufficient amount of the dye liquid must be added so, when the container is placed upside down, the entire seal area must be covered); (c) the container is entirely sealed; (d) the container is placed upside down (i.e. inverted) on the white paper at room temperature; and (e) after 30 minutes, the white paper is inspected to determine if the white paper is contaminated with the blue crystal dye liquid.

The term "air tight" means the moisture ingress of the container (after three days) was less than about 1500 micrograms of water, in another embodiment, about 750 micrograms of water, determined by the following test method: (a) place one gram plus or minus 0.25 grams of molecular sieve in the container and record the weight; (b) the container is closed by applying, in a singular motion, a frontal downward pressure upon the thumb tab until the rim portion, adjacent to the thumb tab, contacts the inside flat part of the cap also adjacent to the thumb tab; (c) place the closed container in an environmental chamber at conditions of 80% relative humidity and 72F.; (c) after one day, weigh the container containing the molecular sieve; (d) after four days, weigh the container containing the molecular sieve; and (e) subtract the first day sample from the fourth day sample to calculate the moisture ingress of the container in units of micrograms of water. Further still, for the purposes of the present application the term "interference fit" means physical contact between two or more components.

BACKGROUND OF THE INVENTION

Many mothers collect and store breast milk for feeding to their babies. Such collection, storage and feeding may typically occur in a hospital setting (e.g., in the case of a premature/low birth weigh baby) or in the home environment (e.g., in the case of a healthy baby released from the hospital shortly after birth).

Of note, the collection of such breast milk may typically be carried out using a breast pump (e.g., manual or electric), the storage of such breast milk may typically be carried out using a storage container and the feeding of such breast milk may typically be carried out using a feeding bottle.

Figure 1:
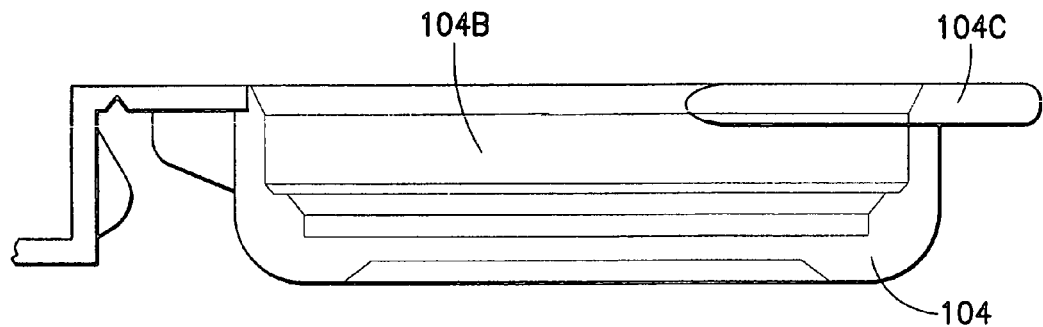
FIG. 1 shows a side view of a cap and top body area according to a first embodiment of the present invention (the size indicators in the drawing are intended to provide an example, and not be restrictive)

Among those benefits and improvements that have been disclosed, other objects and advantages of this invention will become apparent from the following description taken in conjunction with the accompanying figures. The figures constitute a part of this specification and include illustrative embodiments of the present invention and illustrate various objects and features thereof.

DETAILED DESCRIPTION OF THE INVENTION

Detailed embodiments of the present invention are disclosed herein; however, it is to be understood that the disclosed embodiments are merely illustrative of the invention that may be embodied in various forms. In addition, each of the examples given in connection with the various embodiments of the invention are intended to be illustrative, and not restrictive. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

Referring now to FIGS. 1-4, one example of the present invention is shown (of course, the size indicators in the drawings are intended to provide an example, and not be restrictive). More particularly, it is seen that container 100 may be used for collecting and storing breast milk obtained using a breast pump (not shown). In this regard, body 102 may have open end 102A (with lip 102B), closed end 102C and cavity 102D between open end 102A and closed end 102C for receiving therein the breast milk. Further, container 100 may include cap 104 and hinge 106 (disposed, for example, adjacent open end 102A) for connecting cap 104 to body 102. Further still, body 102 may include base 102E (e.g., for providing a stable surface to help prevent tipping over).

Moreover, sealing mechanism 108 may be disposed on cap 104. In one example (which example is intended to be illustrative and not restrictive), sealing mechanism 108 may provide a watertight seal between cap 104 and lip 102B when cap 104 is placed thereon (this watertight seal may be resealable). In another example (which example is intended to be illustrative and not restrictive), sealing mechanism 108 may provide an airtight seal between cap 104 and lip 102B when cap 104 is placed thereon (this airtight seal may be resealable).

Further, at least one thread 110 may be disposed at open end 102A (wherein thread 110 may be configured to provide a screw-on connection between body 102 and the breast pump). In one example (which example is intended to be illustrative and not restrictive), the screw-on connection between body 102 and the breast pump may comprise a watertight seal (this watertight seal may be resealable). In another example (which example is intended to be illustrative and not restrictive), the screw-on connection between body 102 and the breast pump may comprise an airtight seal (this airtight seal may be resealable).

Further still, thread 110 may be configured to provide a screw-on connection (when not connected to the breast pump) between body 102 and a feeding nipple (not shown). In one example (which example is intended to be illustrative and not restrictive), the screw-on connection between body 102 and the feeding nipple may comprise a watertight seal (this watertight seal may be resealable). In another example (which example is intended to be illustrative and not restrictive), the screw-on connection between body 102 and the feeding nipple may comprise an airtight seal (this airtight seal may be resealable).

Referring now more particularly to thread 110, it is noted that in one example (which example is intended to be illustrative and not restrictive), thread 110 may comprise a helical thread running along body 102 from a first position (labeled "a" in FIG. 3, for example) adjacent open end 102A to a second position (labeled "b" in FIG. 3, for example) between open end 102A and closed end 102C.

In another example (which example is intended to be illustrative and not restrictive), the container may comprise a plurality of threads disposed at open end 102A (wherein the plurality of threads are configured to provide a screw-on connection between body 102 and the breast pump and/or feeding nipple).

In another example (which example is intended to be illustrative and not restrictive), each of the plurality of threads may be a helical thread running along body 102 from a respective first position adjacent the open end 102A to a respective second position between open end 102A and closed end 102C.

Figure 2:
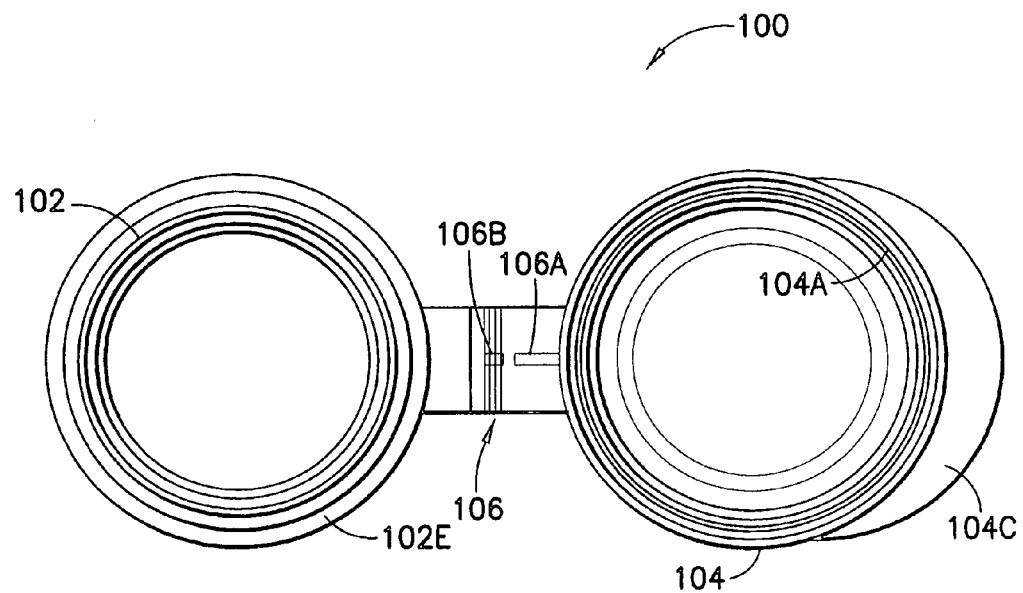
FIG. 2 shows a plan view of a cap and top body area according to the first embodiment of the present invention (the size indicators in the drawing are intended to provide an example, and not be restrictive)
Figure 3:
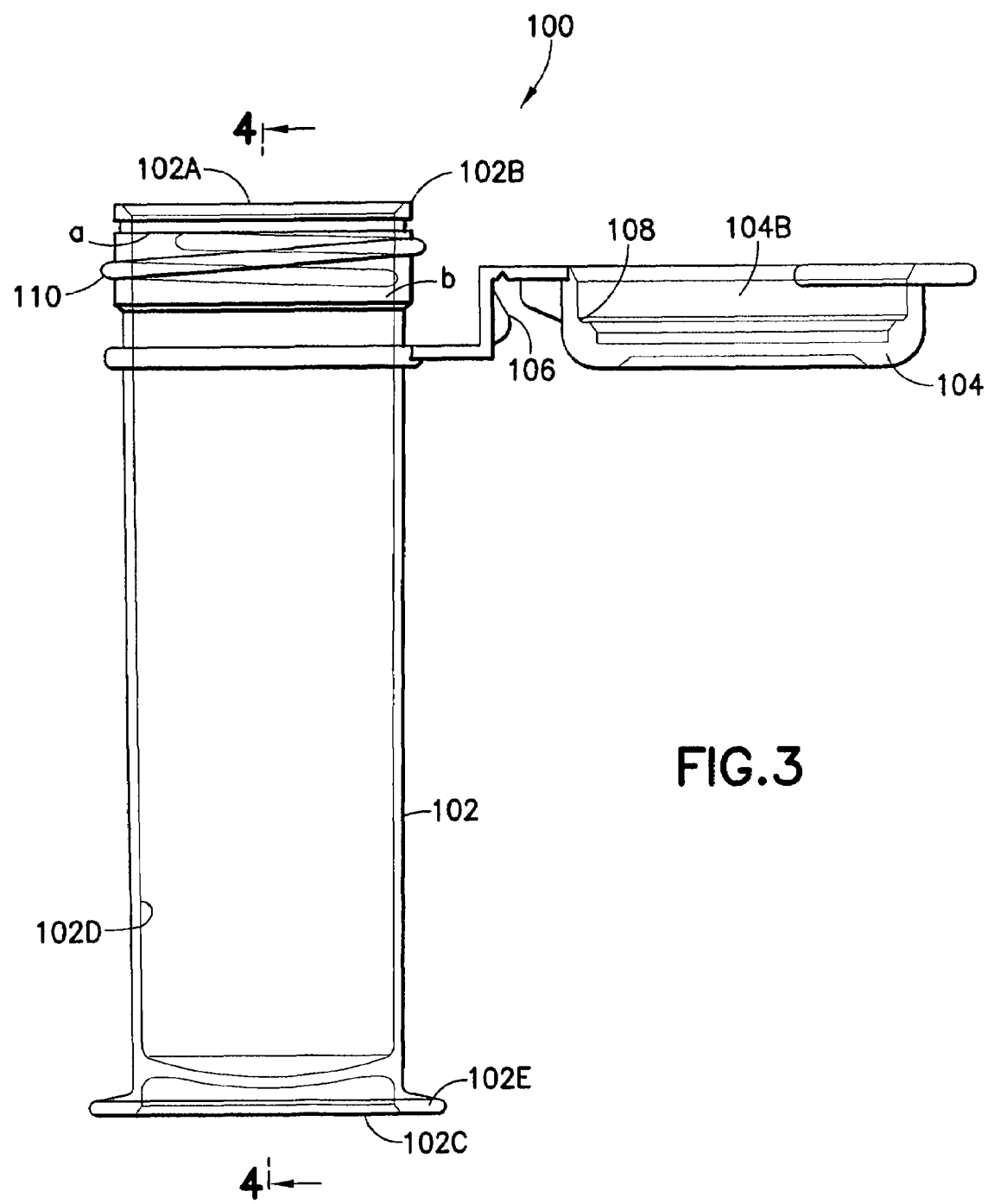
FIG. 3 shows a side view of a container according to the first embodiment of the present invention (the size indicators in the drawing are intended to provide an example, and not be restrictive)
Figure 4:
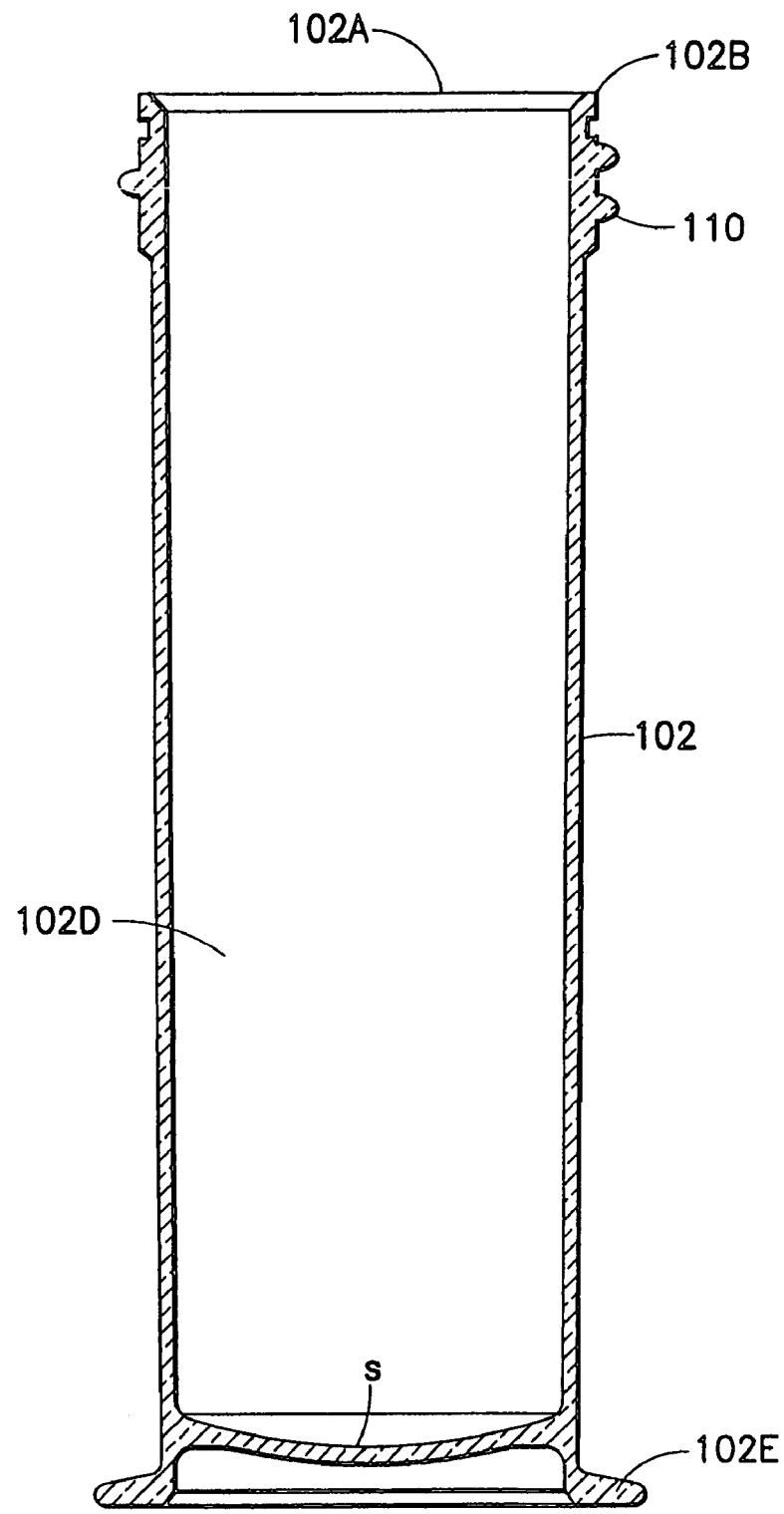
FIG. 4 shows a cross-section taken at line B-B of FIG. 3 (the size indicators in the drawing are intended to provide an example, and not be restrictive)
Figure 5:
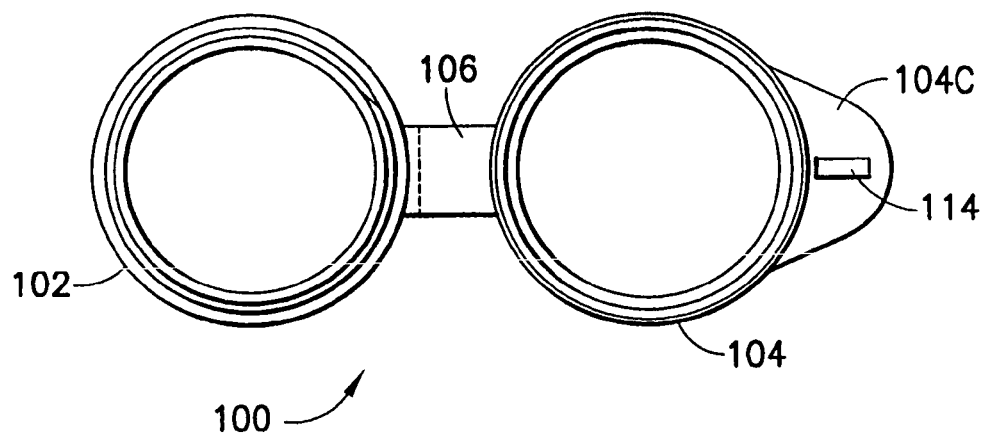
FIG. 5 shows a plan view of a cap and top body area according to a second embodiment of the present invention (the size indicators in the drawing are intended to provide an example, and not be restrictive)
Figure 6:
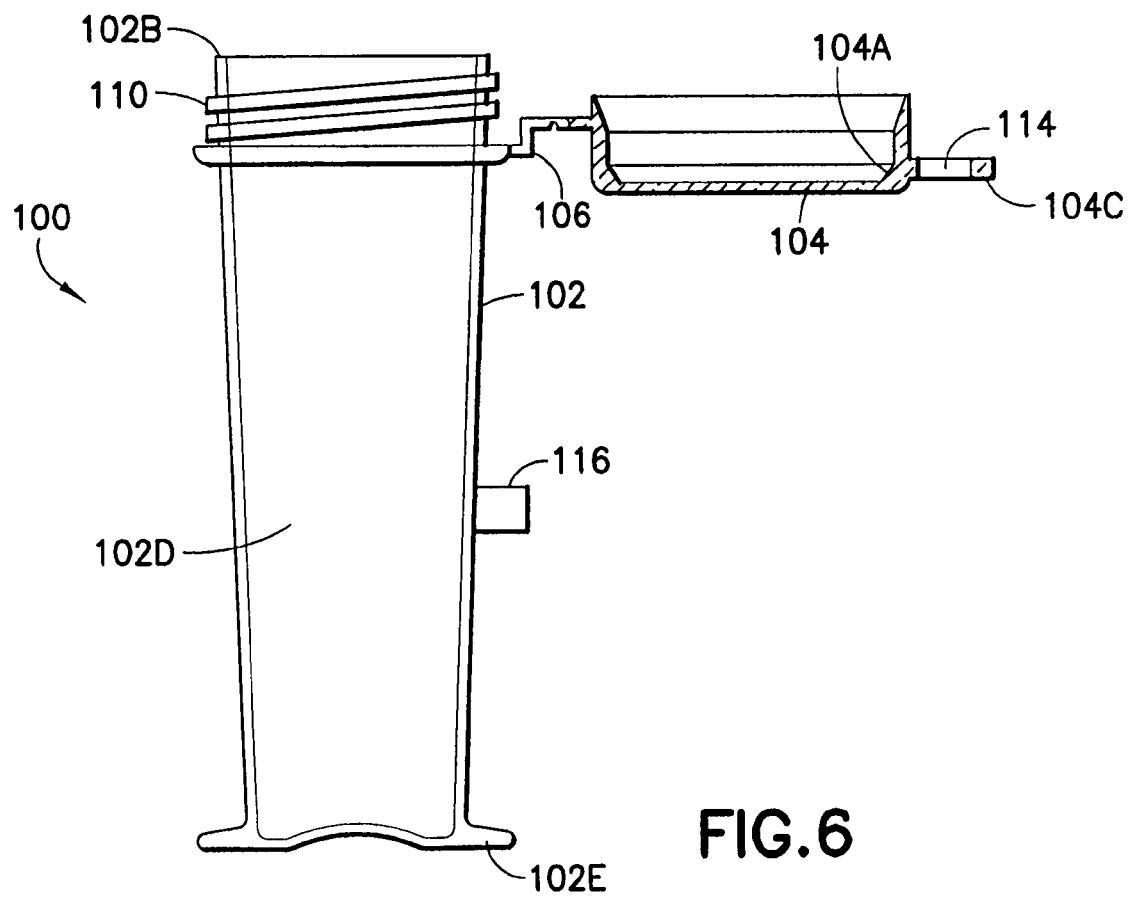
FIG. 6 shows a side view of a container according to the second embodiment of the present invention (the size indicators in the drawing are intended to provide an example, and not be restrictive)
Figure 7:
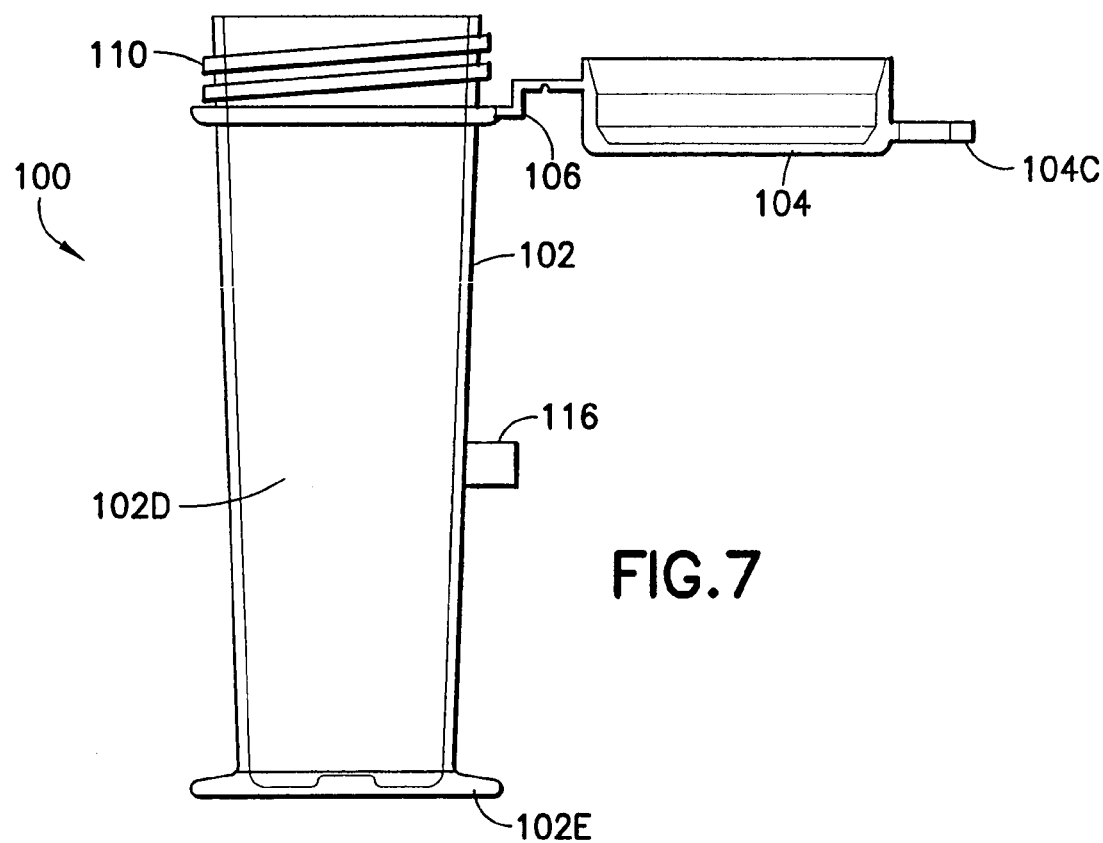
FIG. 7 shows a side view of a container according to the second embodiment of the present invention (the size indicators in the drawing are intended to provide an example, and not be restrictive)
Figure 8:
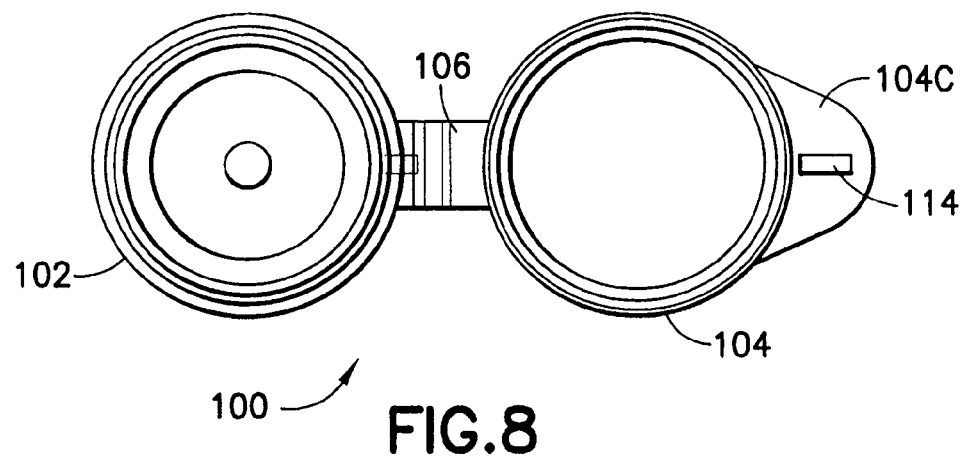
FIG. 8 shows a plan view of a cap and top body area according to the second embodiment of the present invention (the size indicators in the drawing are intended to provide an example, and not be restrictive)
Figure 10:
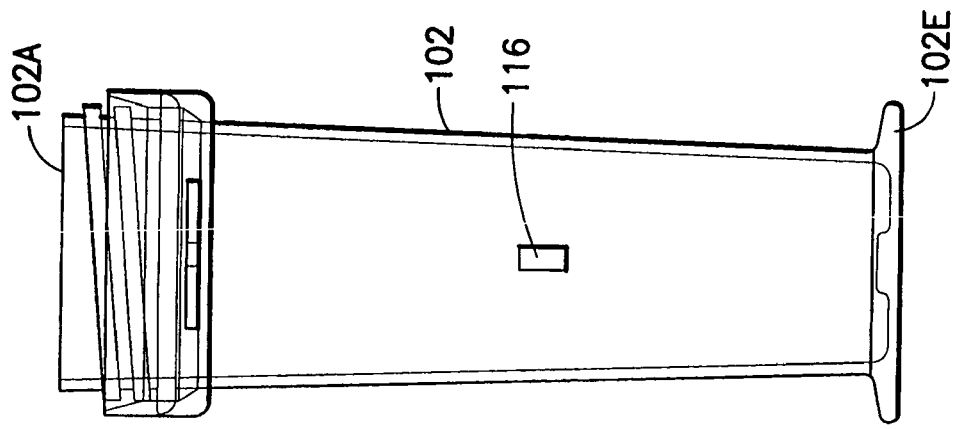
FIG. 10 shows a side view of a container according to the second embodiment of the present invention, wherein this view is offset 90 degrees from the view of FIG. 7 (the size indicators in the drawing are intended to provide an example, and not be restrictive)
Figure 9:
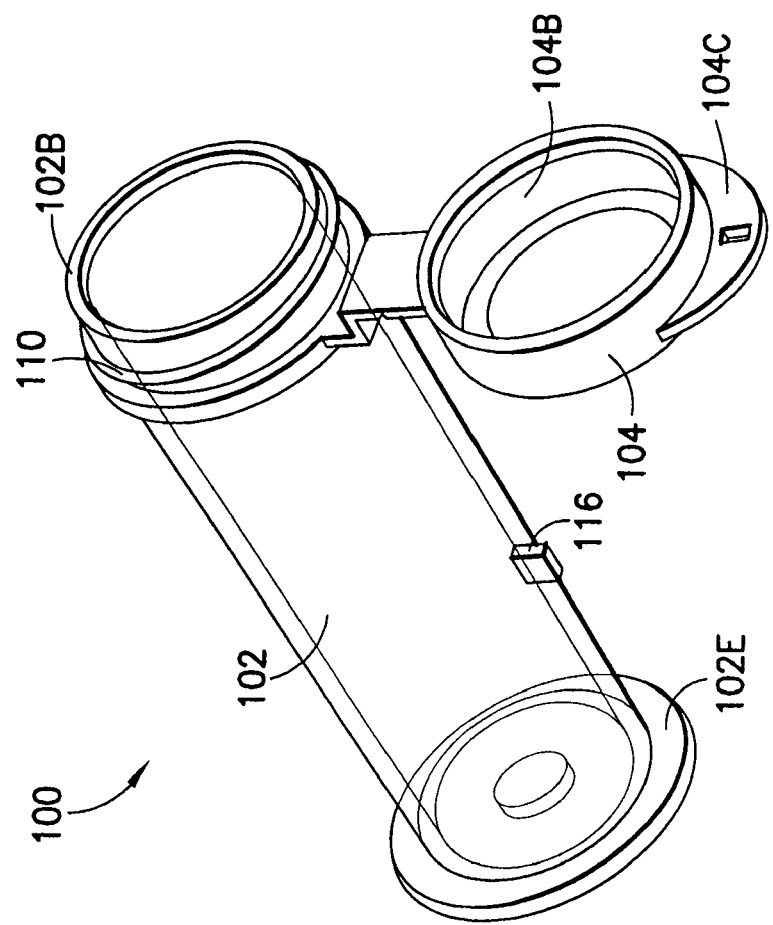
FIG. 9 shows a perspective view of a container according to the second embodiment of the present invention (the size indicators in the drawing are intended to provide an example, and not be restrictive)
Figure 11:
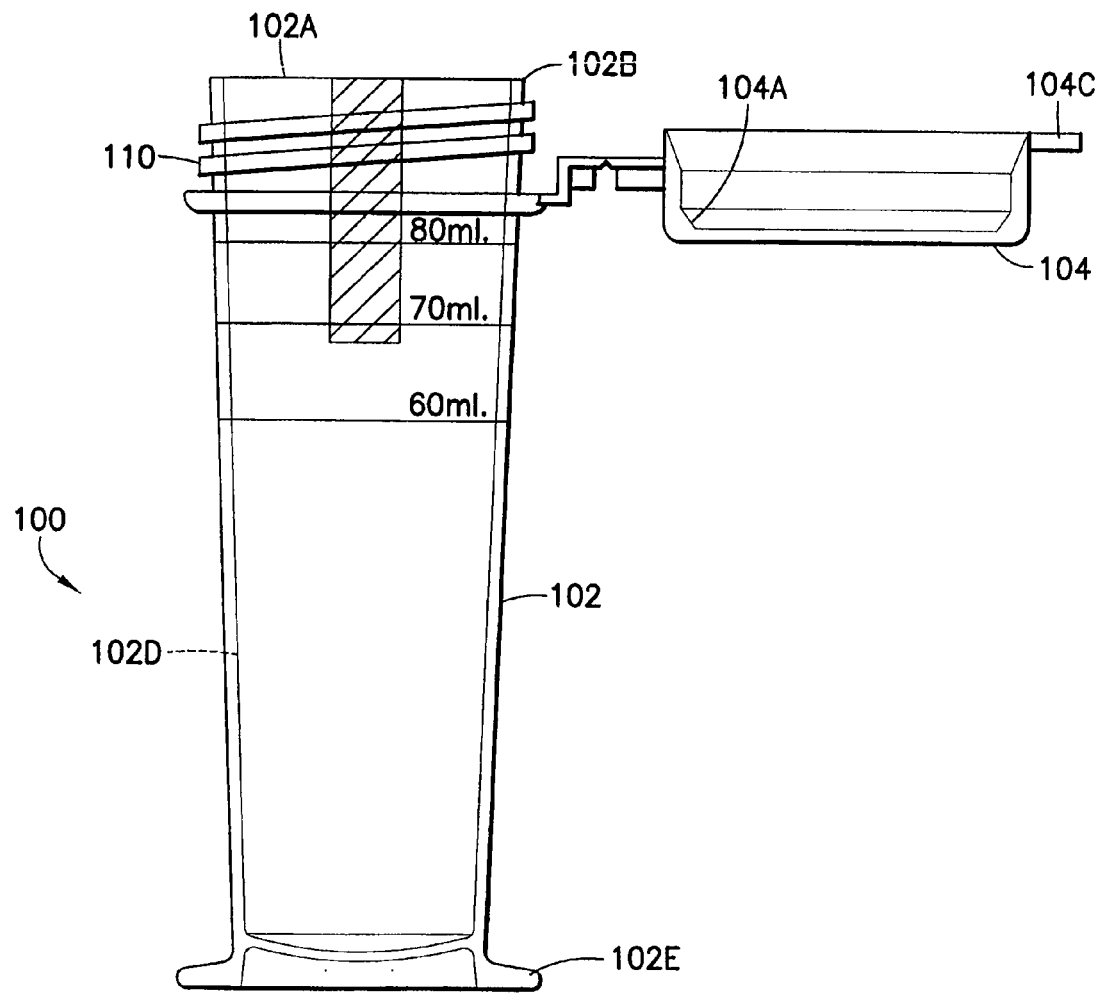
FIG. 11 shows a side view of a container according to a third embodiment of the present invention (the size/volume indicators in the drawing are intended to provide an example, and not be restrictive)
Figure 21:
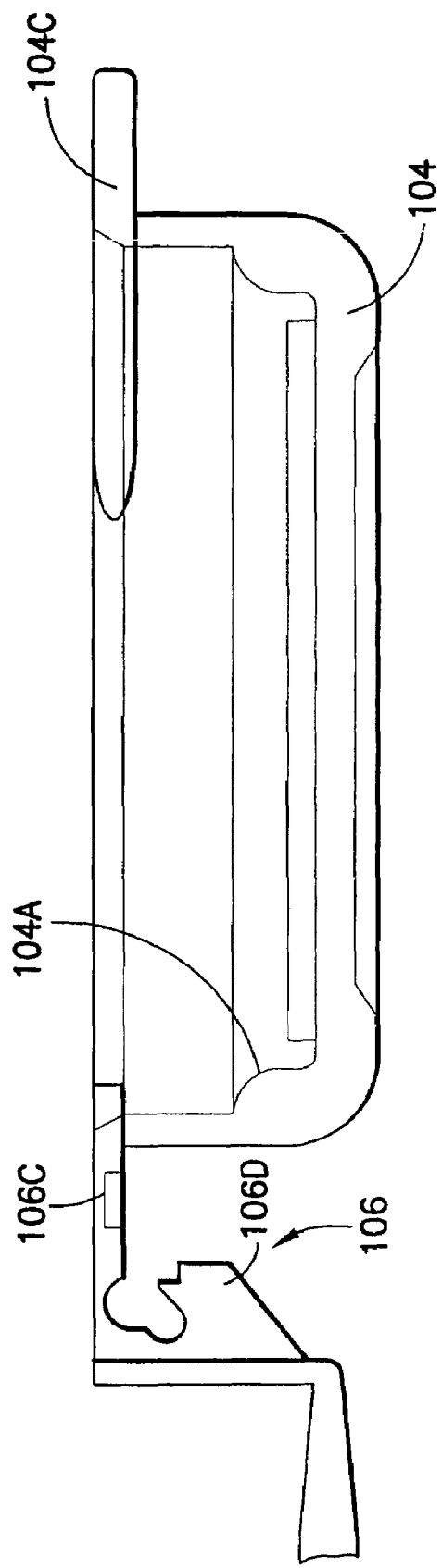
FIG. 21 shows a side view of a cap and hinge according to a seventh embodiment of the present invention (the size indicators in the drawing are intended to provide an example, and not be restrictive)
Figure 22:
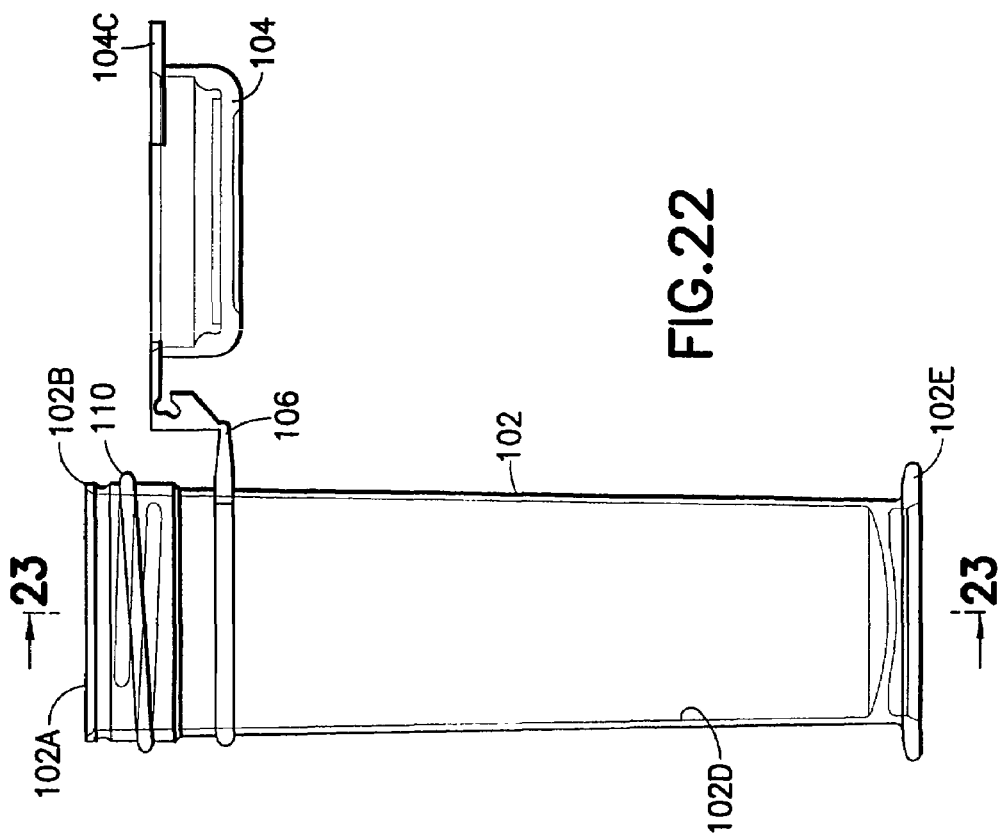
FIG. 22 shows a side view of a container according to the seventh embodiment of the present invention (the size indicators in the drawing are intended to provide an example, and not be restrictive)
Figure 23:
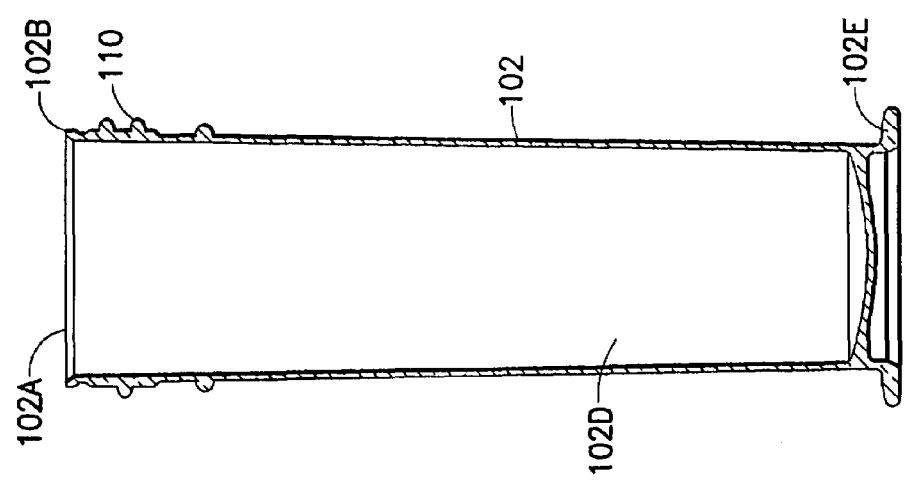
FIG. 23 shows a cross-section taken at line B-B of FIG. 22 (the size indicators in the drawing are intended to provide an example, and not be restrictive)
Figure 24:
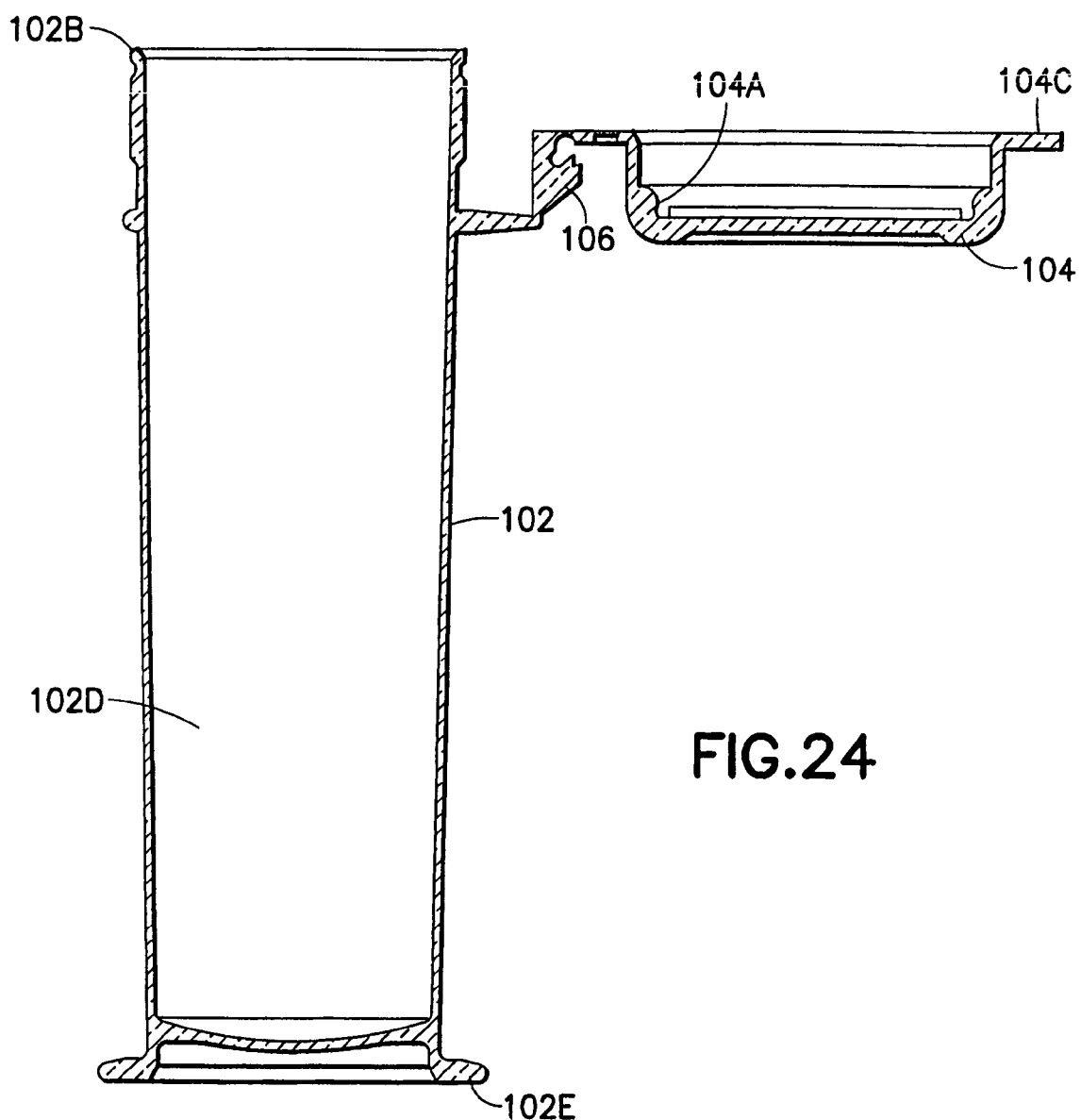
FIG. 24 shows a cross-section offset 90 degrees from FIG. 23 (the size indicators in the drawing are intended to provide an example, and not be restrictive)
Figure 25:
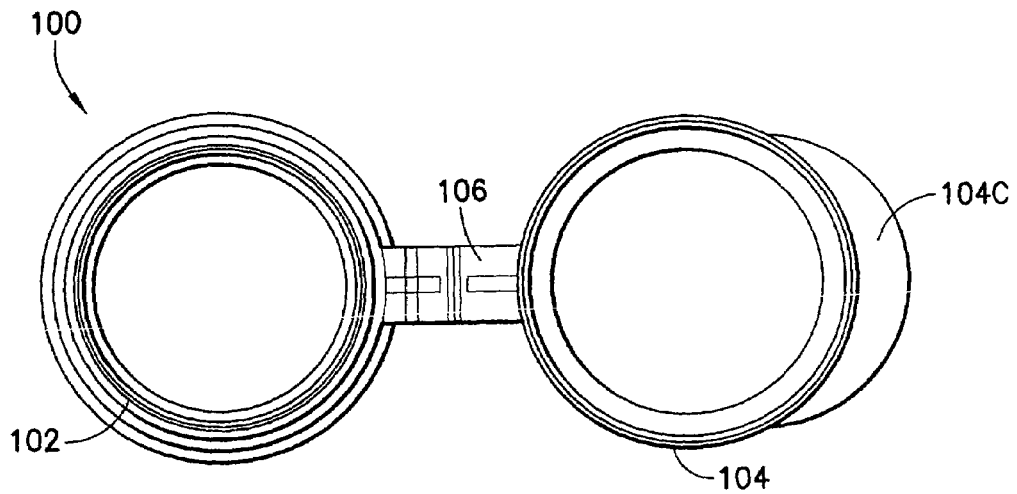
FIG. 25 shows a plan view of a cap and top body area according to an eighth embodiment of the present invention (the size indicators in the drawing are intended to provide an example, and not be restrictive)
Figure 26:
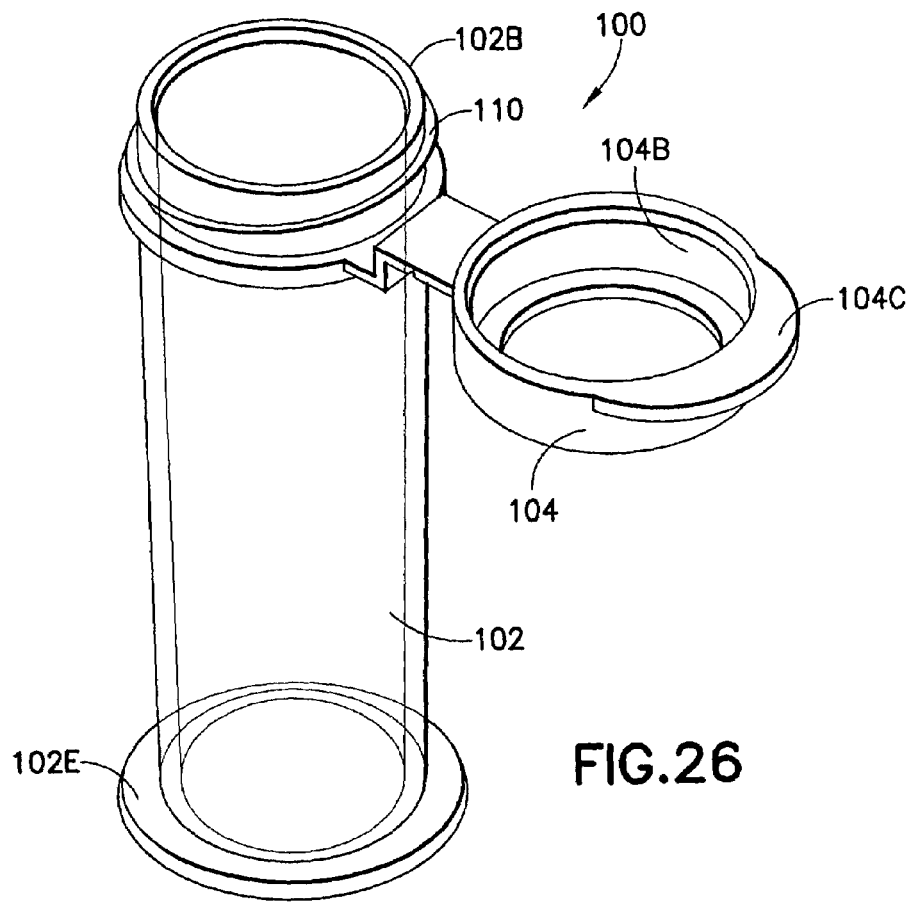
FIG. 26 shows a perspective view of a container according to the eighth embodiment of the present invention (the size indicators in the drawing are intended to provide an example, and not be restrictive)
Figure 27:
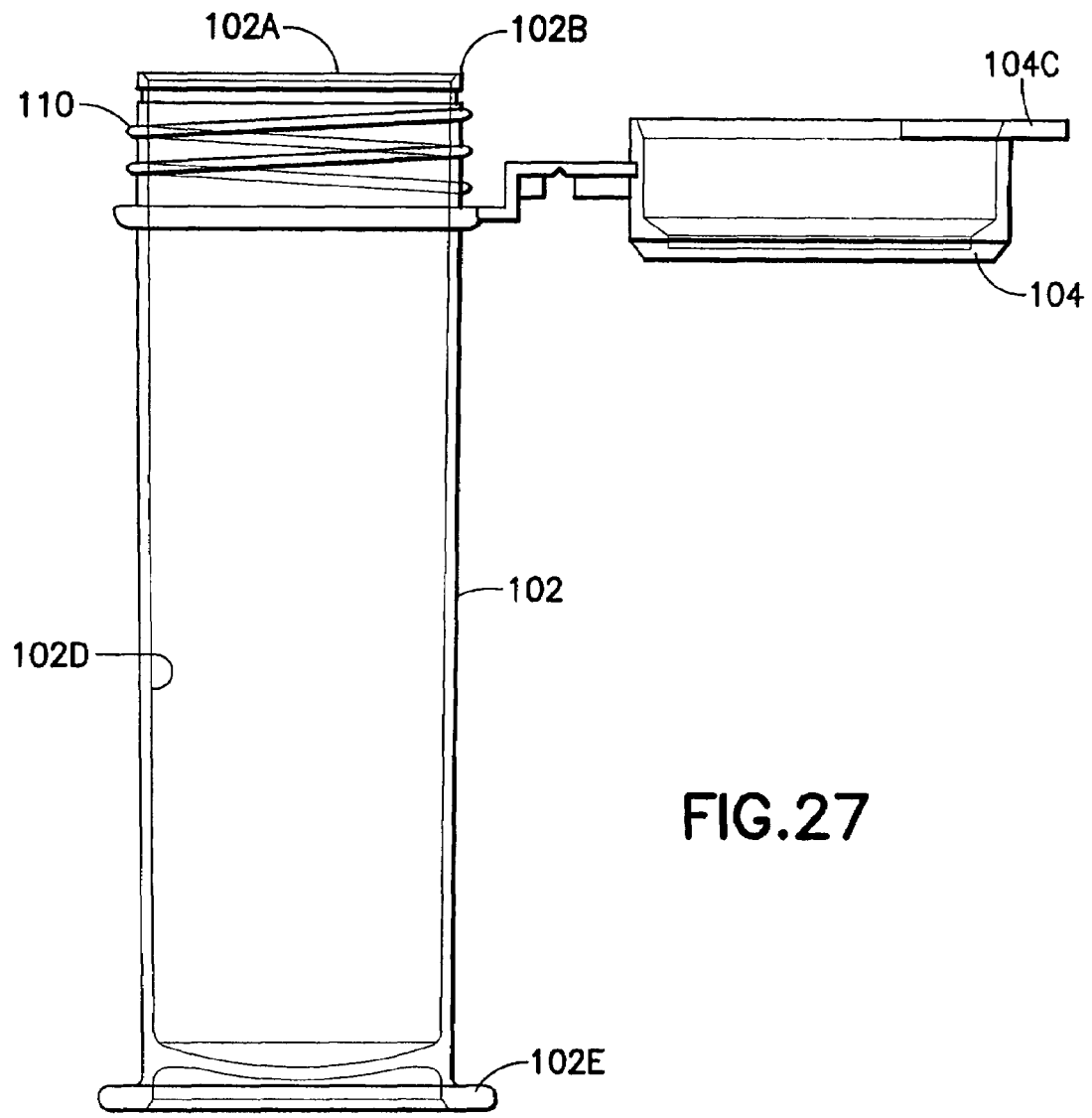
FIG. 27 shows a side view of a container according to the eighth embodiment of the present invention (the size indicators in the drawing are intended to provide an example, and not be restrictive)
Figure 28:
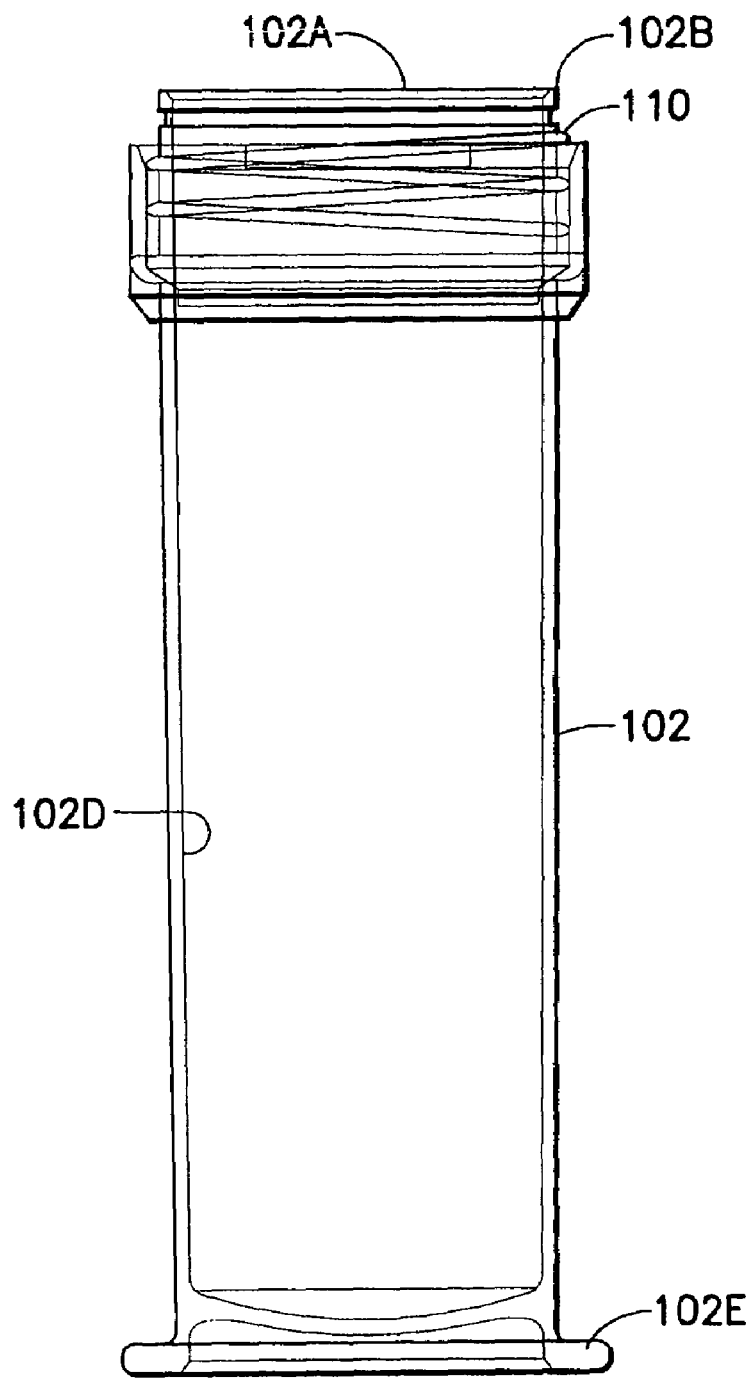
FIG. 28 shows a side view of a container according to the eighth embodiment of the present invention, wherein this view is offset 90 degrees from the view shown in FIG. 27 (the size indicators in the drawing are intended to provide an example, and not be restrictive)
Figure 31:
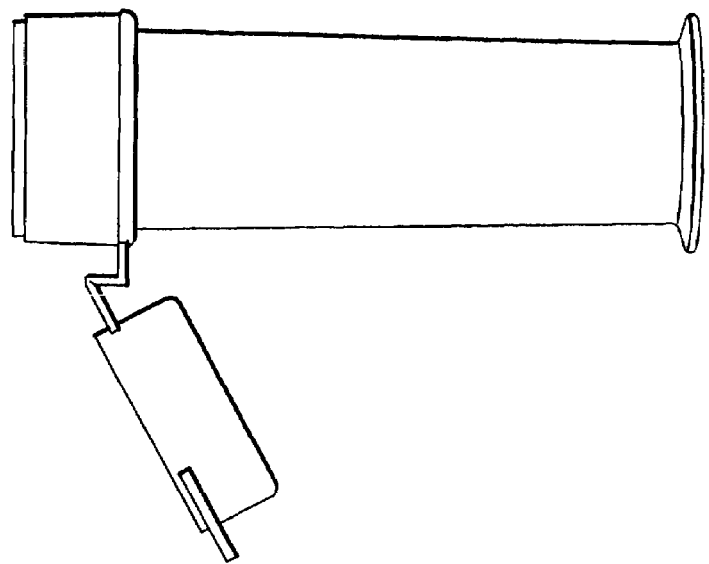
FIG. 31 shows a perspective view of a container according to the ninth embodiment of the present invention, wherein a feeding nipple is attached to the body.
Figure 30:
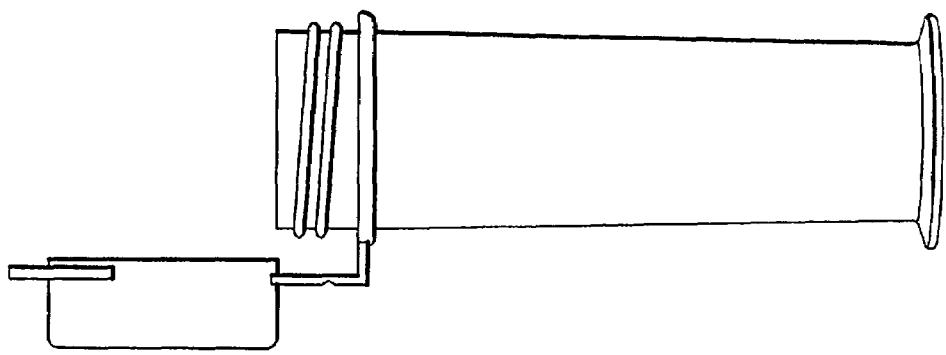
FIG. 30 shows a perspective view of a container according to the ninth embodiment of the present invention, wherein the cap is not sealed to the lip of the body.
Figure 29:
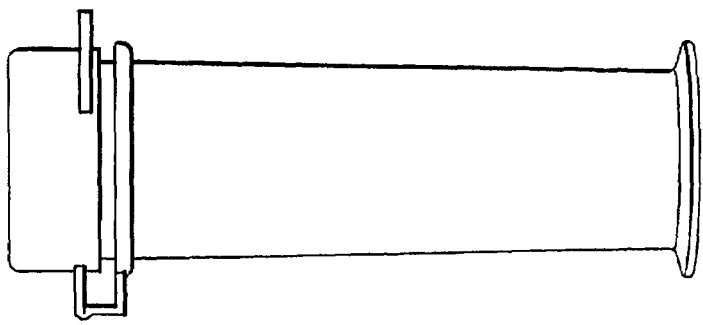
FIG. 29 shows a perspective view of a container according to a ninth embodiment of the present invention, wherein the cap is shown sealed to the lip of the body.

Referring now more particularly to hinge 106, it is noted that in one example (which example is intended to be illustrative and not restrictive), hinge 106 may be configured to be capable of releasably holding cap 104 in an open position, that is, such that cap 104 does not cover open end 102A (see, e.g., mating features 106A and 106B of FIG. 2 and mating features 106C and 106D of FIG. 21). In another example (which example is intended to be illustrative and not restrictive), cap 104 may be held in the open position by a different mechanism (see, e.g., aperture 114 and protrusion 116 of FIGS. 5 and 6).

Referring now more particularly to sealing mechanism 108, it is noted that in one example (which example is intended to be illustrative and not restrictive), this sealing mechanism 108 may comprise groove 104A in cap 104 (wherein groove 104A is configured to form an interference fit with lip 102B).

Referring now more particularly to cap 104, it is noted that in one example (which example is intended to be illustrative and not restrictive), cap 104 may include skirt portion 104B. In another example (which example is intended to be illustrative and not restrictive), skirt portion 104B may be configured to cover at least a portion of thread(s) 110 when cap 104 is placed over open end 102A. In another example (which example is intended to be illustrative and not restrictive), skirt portion 104B may be configured to cover essentially all of thread(s) 110 when cap 104 is placed over open end 102A. In another example (which example is intended to be illustrative and not restrictive), cap 104 may include tab 104C (e.g. a thumb tab) for aiding in opening and closing the cap in an easy and efficient "flip-top" manner.

Suitable material for the container includes plastic (e.g. thermoplastics such as polypropylene and polyethylene). At least some or all of the embodiments of the present invention can be molded according to, for example, techniques disclosed in U.S. Pat. No. Re 37,676 (a reissue of U.S. Pat. No. 5,723,085), U.S. Pat. Nos. 6,303,064, 4,812,116, and 4,783,056, all of which are incorporated herein by reference. In yet another embodiment, the container can be injection blow molded.

Figure 12:
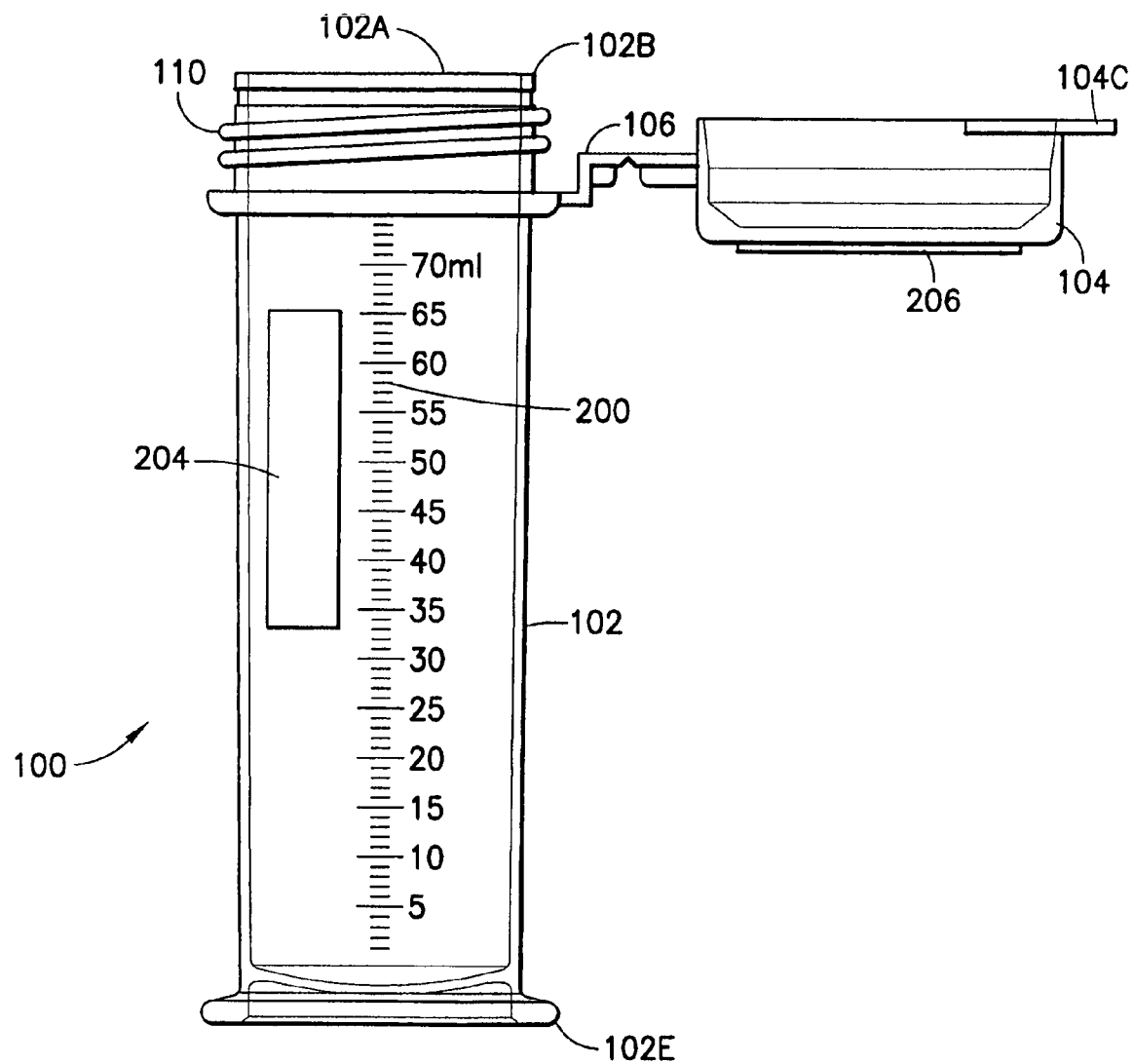
FIG. 12 shows a side view of a container according to a fourth embodiment of the present invention (the size indicators in the drawing are intended to provide an example, and not be restrictive)
Figure 13:
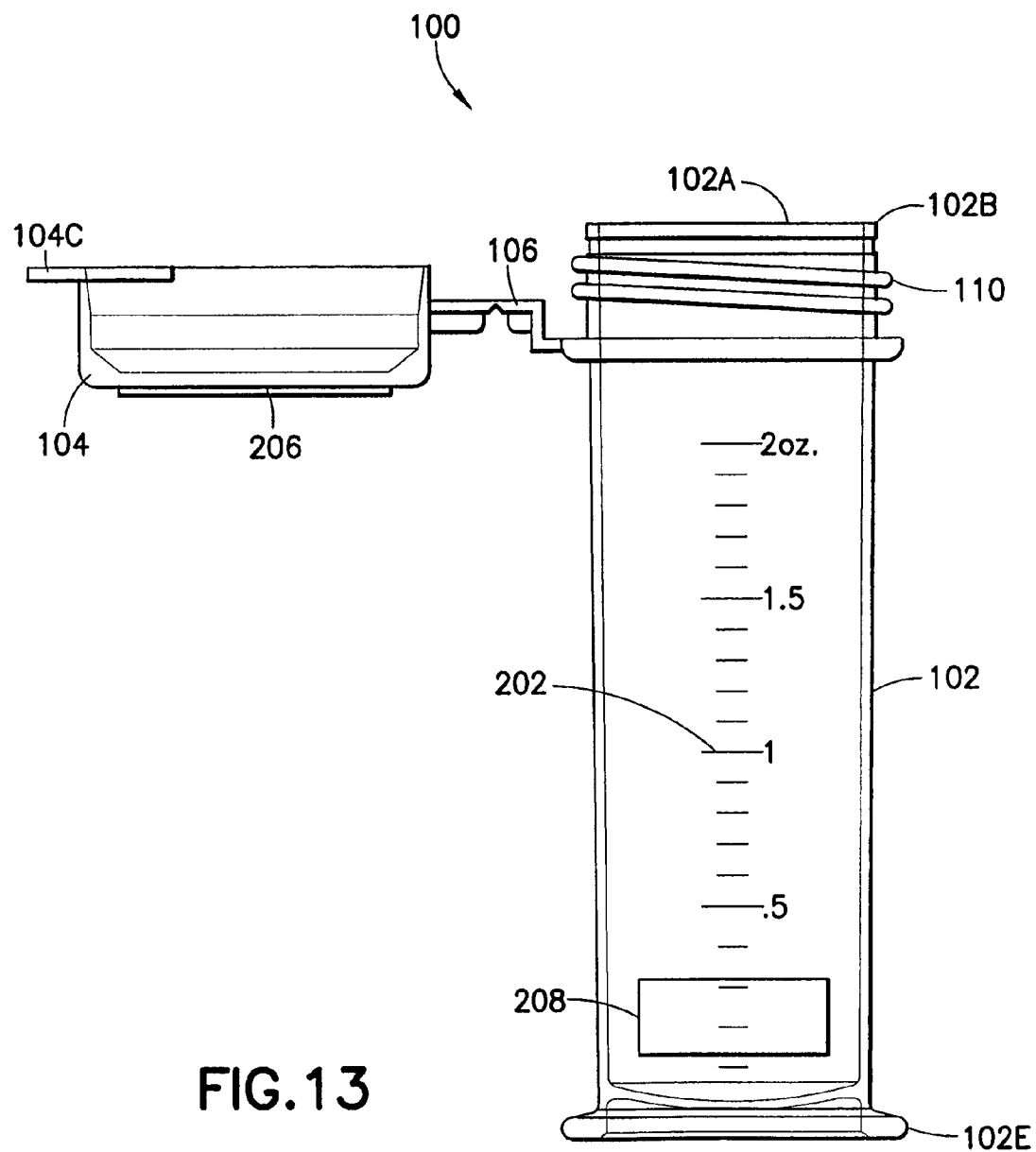
FIG. 13 shows the other side of the container shown in FIG. 12 (the size/volume indicators in the drawing are intended to provide an example, and not be restrictive)
Figure 14:
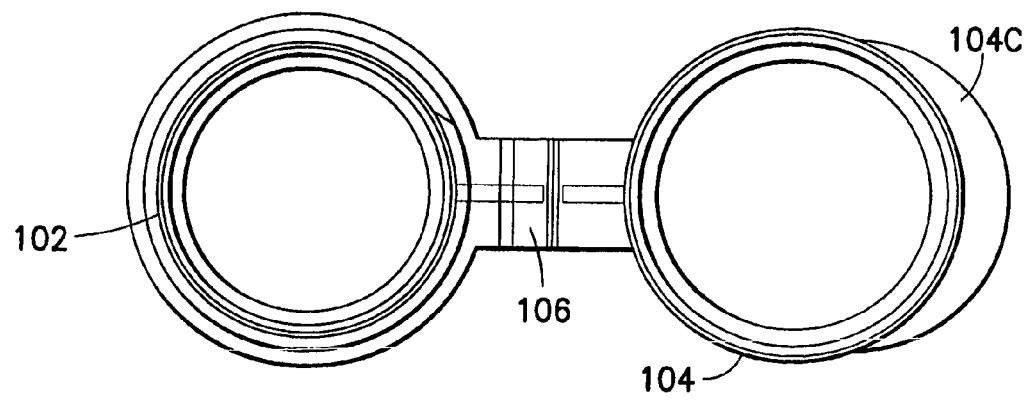
FIG. 14 shows a plan view of a cap and top body area according to a fifth embodiment of the present invention (the size indicators in the drawing are intended to provide an example, and not be restrictive)
Figure 15:
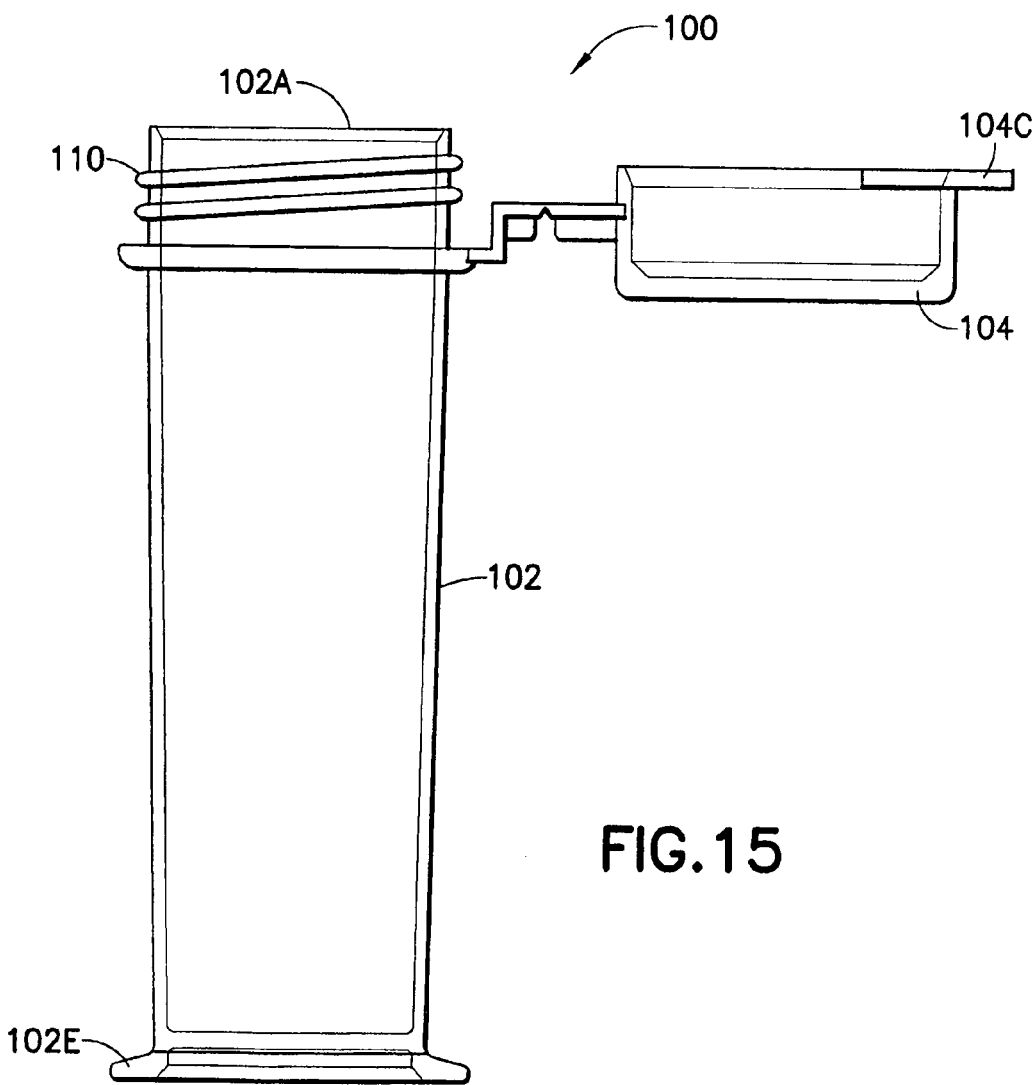
FIG. 15 shows a side view of a container according to the fifth embodiment of the present invention (the size indicators in the drawing are intended to provide an example, and not be restrictive)
Figure 17:
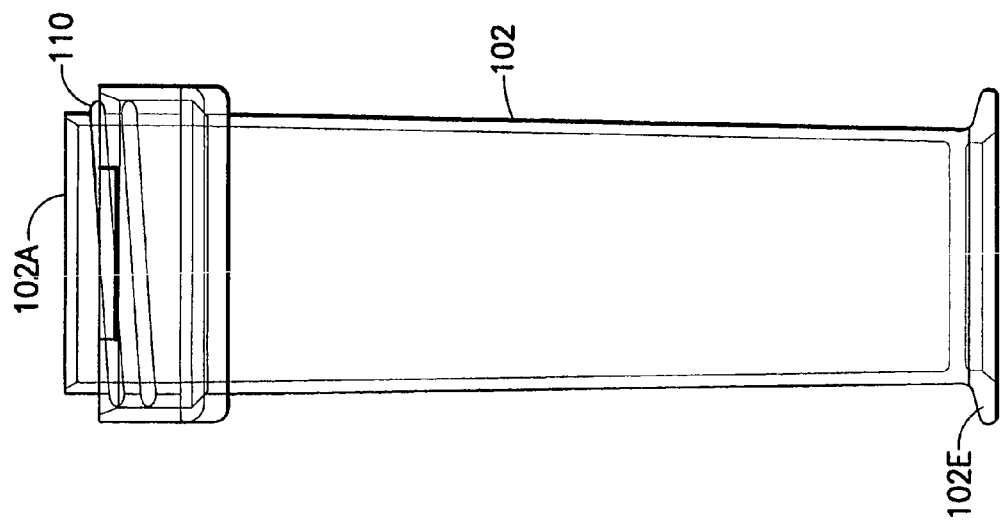
FIG. 17 shows a side view of a container according to the fifth embodiment of the present invention, wherein this view is 90 degrees offset from the view of FIG. 15 (the size indicators in the drawing are intended to provide an example, and not be restrictive)
Figure 16:
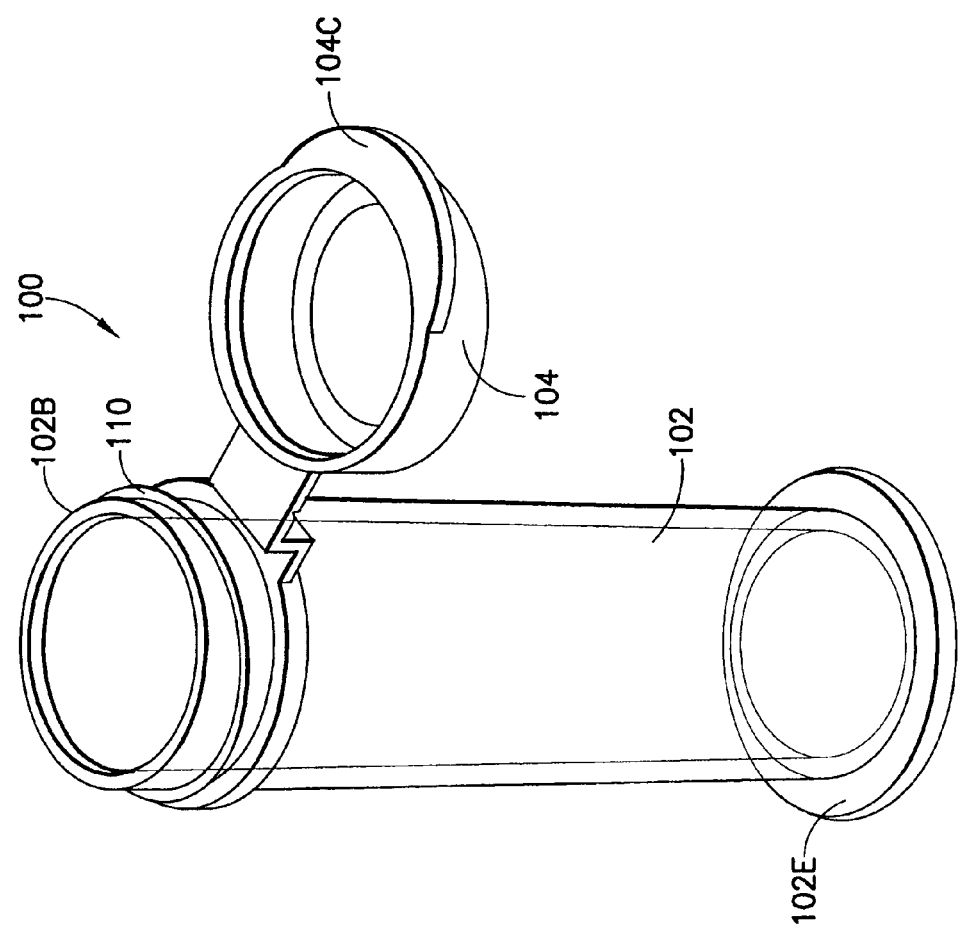
FIG. 16 shows a perspective view of a container according to the fifth embodiment of the present invention (the size indicators in the drawing are intended to provide an example, and not be restrictive)
Figure 18:
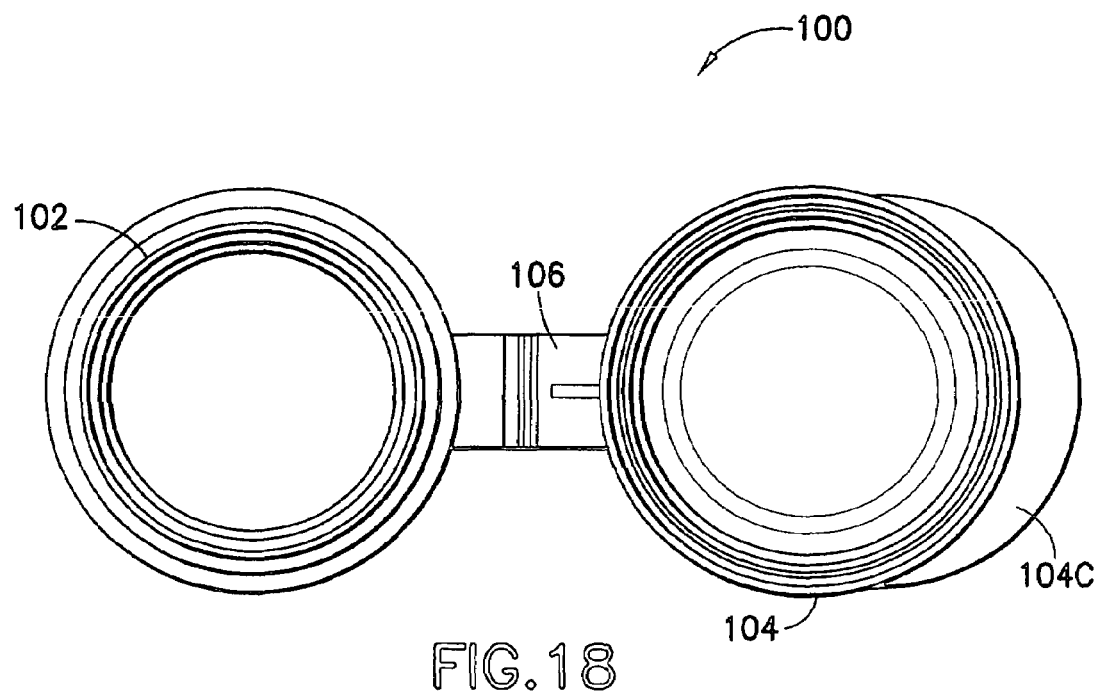
FIG. 18 shows a plan view of a cap and top body area according to a sixth embodiment of the present invention (the size indicators in the drawing are intended to provide an example, and not be restrictive)
Figure 19:
FIG. 19 shows a side view of a top body area according to the sixth embodiment of the present invention, wherein the lip is shown in detail (the size indicators in the drawing are intended to provide an example, and not be restrictive)
Figure 20:
FIG. 20 shows a side view of a top body area according to the sixth embodiment of the present invention, wherein the thread is shown in detail (the size indicators in the drawing are intended to provide an example, and not be restrictive)

In yet another example (which example is intended to be illustrative and not restrictive), the body may include calibration markings (e.g., to indicate the amount of breast milk contained therein, to indicate the amount of breast milk being fed). In this regard, see, for example, FIG. 12 showing calibration markings 200 and FIG. 13 showing calibration markings 202. Of note, the body may be calibrated in any convenient manner for accurate collection/feeding (e.g., calibrated in CC/mls/oz). In one specific example (which example is intended to be illustrative and not restrictive), tick marks may be provided every CC up to 10 and then by every 5 CC's.

In yet another example (which example is intended to be illustrative and not restrictive), the body may contain any convenient amount of milk (e.g., 70 ml, 2.3 oz, 2 oz, 4 oz, 8 oz).

In yet another example (which example is intended to be illustrative and not restrictive), the exterior of the container may be of any convenient size (e.g., for storage in a refrigerator or freezer).

In yet another example (which example is intended to be illustrative and not restrictive), at least one of the body and the cap may include an area thereon configured to receive writing. In this regard, see, for example, writing area 204 and 206 of FIG. 12 and writing area 208 and 206 of FIG. 13. Of note, the body and/or cap may contain one or more areas to write appropriate information such as, for example, mother's name, baby's name, collection date/time, any illnesses, any use of medications and/or hospital identification.

In yet another example (which example is intended to be illustrative and not restrictive), at least one of the body, the hinge and the cap may comprise polypropylene (which is believed to essentially not bind and hold fat during storage and which is believed to be FDA approved for food contact and storage). In another example (which example is intended to be illustrative and not restrictive), polycarbonate may be used in the construction of the container.

In yet another example (which example is intended to be illustrative and not restrictive), the body, the hinge and the cap may be formed as an integral unit (e.g., so that the cap does not fall on the floor or get lost). In this regard, see, for example, hinge 106 connecting body 102 to cap 104 in FIGS. 1-4.

In yet another example (which example is intended to be illustrative and not restrictive), the body and/or the cap may be transparent or translucent (e.g., for easy viewing of breast milk volume). In still another example (which example is intended to be illustrative and not restrictive), the body and/or the cap may be colored. In still yet another example (which example is intended to be illustrative and not restrictive), the body may be transparent or translucent while the cap is colored.

In yet another example (which example is intended to be illustrative and not restrictive), the watertight and/or airtight seals provided by the present invention may help maximize shelf-life in storage.

In yet another example (which example is intended to be illustrative and not restrictive), the thread(s) may fit standard breast pumps and/or feeding nipples. In this regard, see, for example, thread 110 of FIGS. 12 and 13.

In yet another example (which example is intended to be illustrative and not restrictive), the container may be manufactured in an FDA inspected and approved facility.

In yet another example (which example is intended to be illustrative and not restrictive), the container may be ready to use (e.g., sterile or aseptic by manufacturing process).

In yet another example (which example is intended to be illustrative and not restrictive), the container may be freezable and/or microwavable and/or autoclavable).

In yet another example (which example is intended to be illustrative and not restrictive), the cap may be designed to reduce the risk of contamination (e.g., the cap may be detachable and/or may have a long skirt to protect the inside). With regard to a detachable cap, this may, of course, be accomplished, for example, by eliminating hinge 106. With regard to the long skirt, see, for example, skirt portion 104B of FIGS. 1 and 3.

In yet another example (which example is intended to be illustrative and not restrictive), the cap may be designed to face away from the mother's body during collection.

In yet another example (which example is intended to be illustrative and not restrictive), the cavity in the body may have a concave, conical and/or skirted bottom (e.g., to get out small amounts of breast milk). In this regard, see, for example, the curved bottom surface "S" of FIG. 4.

In yet another example (which example is intended to be illustrative and not restrictive), the container may be designed to permit withdrawal of breast milk from the bottom (e.g., so that a clinician may withdraw the contents from the bottom of a 2 oz bottle with a 3-inch syringe).

In yet another example (which example is intended to be illustrative and not restrictive), the container may provide any convenient amount of head space (e.g., for collecting milk).

In yet another example (which example is intended to be illustrative and not restrictive), the container may connect to an electric breast pump and/or a manual breast pump.

In yet another example (which example is intended to be illustrative and not restrictive), the container may comprise any material which will render the container hard-sided.

Referring now to FIGS. 5-31, various views of other examples of containers according to the present invention are shown.

While a number of embodiments of the present invention have been described, it is understood that these embodiments are illustrative only, and not restrictive, and that many modifications may become apparent to those of ordinary skill in the art. For example, the container may be made by any desired manufacturing method (e.g., being formed in a one-piece or multi-piece mold; being formed with two shot injection molding). Further, the various steps may be carried out in any desired order (and any desired steps may be added and/or deleted).

What is claimed is:

1. A container for collecting and storing breast milk obtained using a breast pump, comprising:
    a body, wherein the body has an open end with a lip, a closed end and a cavity between the open end and the closed end for receiving therein the breast milk;
    an unthreaded cap;
    a hinge disposed adjacent the open end of the body for integrally connecting the cap to the body so that the body, hinge and cap are a unitary structure;
    a sealing mechanism disposed on the cap, wherein the sealing mechanism provides a resealable, watertight seal between the cap and the lip of the body when the cap is placed thereon; and
    at least one thread disposed at the open end of the body, wherein the thread is configured to provide a screw-on connection between the body and the breast pump.

2. The container of claim 1, wherein the screw-on connection is configured to provide a watertight seal between the body and the breast pump.

3. The container of claim 1, wherein the sealing mechanism provides an airtight seal between the cap and the lip of the body when the cap is placed thereon.

4. The container of claim 1, wherein the screw-on connection is configured to provide an airtight seal between the body and the breast pump.

5. The container of claim 1, wherein the thread is configured to provide a screw-on connection between the body and a feeding nipple.

6. The container of claim 5, wherein the screw-on connection is configured to provide a watertight seal between the body and the feeding nipple.

7. The container of claim 6, wherein the screw-on connection is configured to provide an airtight seal between the body and the feeding nipple.

8. The container of claim 1, wherein the at least one thread is a helical thread running along the body from a first position adjacent the open end to a second position between the open end and the closed end.

9. The container of claim 1, wherein the at least one thread comprises a plurality of threads disposed at the open end of the body, wherein the plurality of threads are configured to provide a screw-on connection between the body and the breast pump.

10. The container of claim 9, wherein each thread is a helical thread running along the body from a respective first position adjacent the open end to a respective second position between the open end and the closed end.

11. The container of claim 1, wherein the hinge is articulated at one position.

12. The container of claim 1, wherein the hinge is configured to be capable of holding the cap in an open position, such that the cap does not cover the open end of the body.

13. The container of claim 1, wherein the sealing mechanism includes a groove in the cap configured to form an interference fit with the lip of the body.

14. The container of claim 1, wherein the cap includes a skirt portion.

15. The container of claim 14, wherein the skirt portion is configured to cover at least a portion of the thread when the cap is placed over the open end of the body.

16. The container of claim 15, wherein the skirt portion is configured to cover essentially all of the thread when the cap is placed over the open end of the body.

17. The container of claim 1, wherein the body includes calibration markings to indicate the amount of breast milk contained therein.

18. The container of claim 1, wherein at least one of the body and the cap includes an area thereon configured to receive writing.

19. The container of claim 1, wherein at least one of the body, the hinge and the cap comprises polypropylene.

20. The container of claim 1, wherein each of the body, the hinge and the cap comprises polypropylene.

21. A container for collecting breast milk obtained using a breast pump and for feeding the breast milk to a baby using a feeding nipple, comprising:
    a body, wherein the body has an open end with a lip, a closed end and a cavity between the open end and the closed end for receiving therein the breast milk from the breast pump;
    an unthreaded cap;
    a hinge disposed adjacent the open end of the body for integrally connecting the cap to the body so that the body, hinge and cap are a unitary structure;
    a sealing mechanism disposed on the cap, wherein the sealing mechanism provides a resealable, watertight seal between the cap and the lip of the body when the cap is placed thereon; and
    at least one thread disposed at the open end of the body, wherein the thread is configured to provide a screw-on connection between the body and the breast pump when collecting the breast milk and a screw-on connection between the body and the feeding nipple when feeding the breast milk.

* * * * *